(12) United States Patent
Foster et al.

(10) Patent No.: US 9,480,834 B2
(45) Date of Patent: Nov. 1, 2016

(54) MULTIPOLAR CONDUCTOR FOR AN IMPLANTABLE MEDICAL DEVICE

(71) Applicant: Cardiac Pacemakers, Inc., St. Paul, MN (US)

(72) Inventors: Arthur J. Foster, Blaine, MN (US); Matthew J. Miller, Stillwater, MN (US); Christopher R. Perrey, Victoria, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 280 days.

(21) Appl. No.: 13/832,515

(22) Filed: Mar. 15, 2013

(65) Prior Publication Data

US 2013/0304170 A1 Nov. 14, 2013

Related U.S. Application Data

(60) Provisional application No. 61/644,157, filed on May 8, 2012.

(51) Int. Cl.
*A61N 1/05* (2006.01)

(52) U.S. Cl.
CPC ............... *A61N 1/05* (2013.01); *A61N 1/056* (2013.01); *A61N 1/0551* (2013.01)

(58) Field of Classification Search
CPC .... A61N 1/05; A61N 1/0551; A61N 1/0534; A61N 1/375; A61N 1/0529; A61N 1/3605; A61N 1/3752; A61N 1/08; A61N 1/3606; A61B 5/042
USPC .................................................. 607/115–116
See application file for complete search history.

(56) References Cited

U.S. PATENT DOCUMENTS

| | | | |
|---|---|---|---|
| 3,890,977 A | 6/1975 | Wilson | |
| 4,365,639 A | 12/1982 | Goldreyer | |
| 4,386,615 A | 6/1983 | Sowton | |
| 4,608,986 A | 9/1986 | Beranek et al. | |
| 5,251,643 A | 10/1993 | Osypka | |
| 5,935,159 A * | 8/1999 | Cross, Jr. | A61N 1/056 607/116 |
| 6,501,991 B1 * | 12/2002 | Honeck | A61N 1/056 607/122 |
| 2002/0095202 A1 * | 7/2002 | Schmidt | A61B 5/0422 607/122 |
| 2010/0016935 A1 * | 1/2010 | Strandberg | A61N 1/056 607/116 |
| 2012/0165902 A1 * | 6/2012 | Sommer | A61N 1/056 607/60 |
| 2012/0265281 A1 * | 10/2012 | Osypka | A61N 1/056 607/127 |

* cited by examiner

*Primary Examiner* — Michael Kahelin
*Assistant Examiner* — Minh Duc Pham
(74) *Attorney, Agent, or Firm* — Faegre Baker Daniels LLP

(57) ABSTRACT

A medical device lead includes a flexible body having a proximal region with a proximal end, and a distal region with a distal end. A connector is coupled to the proximal end of the flexible body of the lead to electrically and mechanically connect the lead to an implantable pulse generator. A composite wire having a proximal end is electrically coupled to the connector. The composite wire includes an inner conductor element and a plurality of outer conductor elements adjacent to and radially spaced from the inner conductor element. A distal end of each of the inner conductor element and the plurality of outer conductor elements is connected to one of a plurality of electrodes in the distal region of the flexible body.

13 Claims, 7 Drawing Sheets

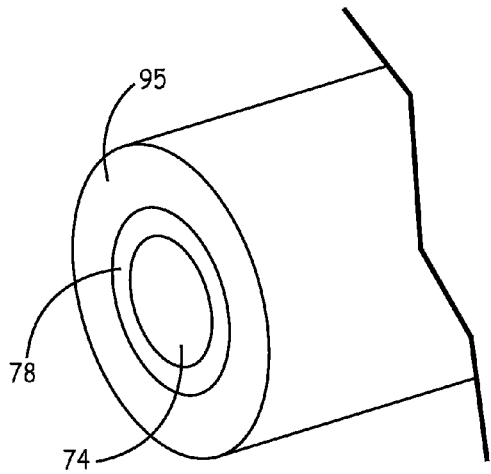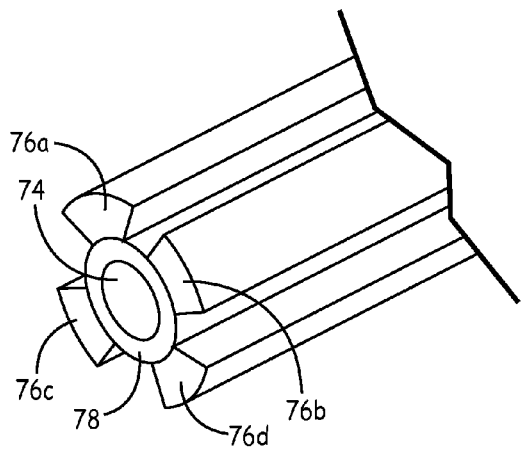
FIG. 6A    FIG. 6B
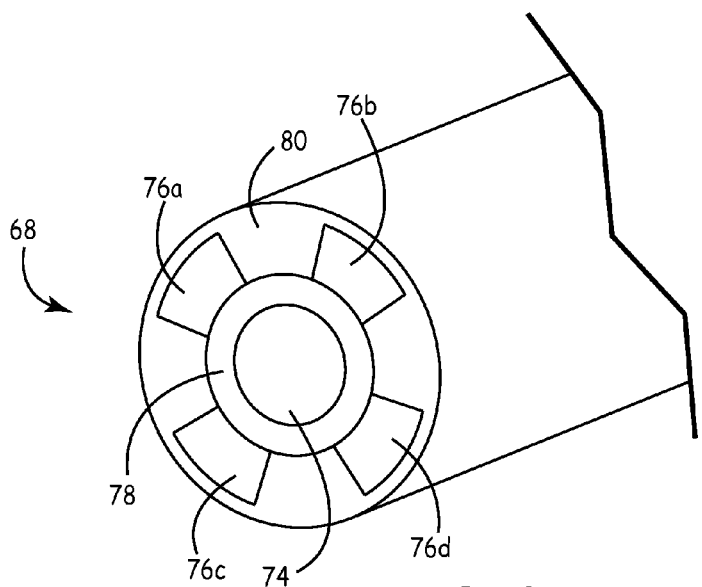
FIG. 6C

MULTIPOLAR CONDUCTOR FOR AN IMPLANTABLE MEDICAL DEVICE

CROSS-REFERENCE TO RELATED APPLICATION

This application claims the benefit of Provisional Application No. 61/644,157, filed May 8, 2012, which is herein incorporated by reference in its entirety.

TECHNICAL FIELD

The present disclosure relates to implantable medical devices. More particularly, the present disclosure relates to a multipolar conductor for an implantable medical device.

BACKGROUND

Various physiological functions can be managed and/or monitored using medical devices. Many such medical devices include conductor elements, where the conductor elements are configured to deliver an electrical signal to a target location within the body and/or sense an electrical signal at a target location within the body. For example, implantable medical devices have been used in association with cardiac rhythm management, which can include cardiac pacing, cardiac defibrillation, and/or cardiac therapy, among other procedures.

SUMMARY

Disclosed herein are various embodiments of a medical device lead including a multipolar conductor, as well as medical device systems including such a lead and methods for making the multipolar conductor.

In Example 1, a medical device lead includes a flexible body having a proximal region with a proximal end, and a distal region with a distal end. A connector is coupled to the proximal end of the flexible body of the lead to electrically and mechanically connect the lead to an implantable pulse generator. A composite wire having a proximal end is electrically coupled to the connector. The composite wire includes an inner conductor element and a plurality of outer conductor elements adjacent to and radially spaced from the inner conductor element. A distal end of each of the inner conductor element and the plurality of outer conductor elements is connected to one of a plurality of electrodes in the distal region of the flexible body.

In Example 2, the medical device lead according to Example 1, wherein each of the plurality of outer conductor elements is substantially parallel to an axis of the inner conductor element.

In Example 3, the medical device lead according to either Example 1 or 2, wherein each of the plurality of outer conductor elements includes an inner arc adjacent to the inner conductor element and an outer arc on a side opposite the inner arc.

In Example 4, the medical device lead according to Example 3, wherein a length of the inner arc is less than a length of the outer arc.

In Example 5, the medical device lead according to any of Examples 1-4, and further comprising an insulative layer between the inner conductor elements and each of the plurality of outer conductor elements.

In Example 6, the medical device lead according to any of Examples 1-5, and further comprising an encapsulating insulator that covers the plurality of outer conductor elements to electrically isolate the plurality of outer conductor elements from each other.

In Example 7, the medical device lead according to any of Examples 1-6, wherein the connector comprises a feedthrough, and wherein a proximal end of each of the plurality of outer conductor elements is axially staggered on a proximal side of the feedthrough.

In Example 8, a composite wire for an implantable medical device includes an inner conductor element and a plurality of outer conductor elements adjacent to and radially spaced from the inner conductor element. A distal end of each of the inner conductor element and the plurality of outer conductor elements is configured for connection to an electrode.

In Example 9, the composite wire according to Example 8, wherein each of the plurality of outer conductor elements is substantially parallel to an axis of the inner conductor element.

In Example 10, the composite wire according to either Example 8 or 9, wherein each of the plurality of outer conductor elements includes an inner arc adjacent to the inner conductor element and an outer arc on a side opposite the inner arc.

In Example 11, the composite wire according to Example 10, wherein a length of the inner arc is less than a length of the outer arc.

In Example 12, the composite wire according to any of Examples 8-11, and further comprising an insulative layer between the inner conductor elements and each of the plurality of outer conductor elements.

In Example 13, the composite wire according to any of Examples 8-12, and further comprising an encapsulating insulator that covers the plurality of outer conductor elements to electrically isolate the plurality of outer conductor elements from each other.

In Example 14, the composite wire according to any of Examples 8-13, wherein the encapsulating insulator has an outer diameter of less than about 0.26 inch (0.66 mm).

In Example 15, the composite wire according to any of Examples 8-14, wherein the inner conductor element has a diameter of less than about 0.003 inch (0.0762 mm) and plurality of outer conductor elements has a height of less than about 0.010 inch (0.254 mm).

In Example 16, a medical device lead includes a flexible body having a proximal region with a proximal end, and a distal region with a distal end. A connector is coupled to the proximal end of the flexible body of the lead to electrically and mechanically connect the lead to an implantable pulse generator. The lead also includes a coil conductor having a proximal end electrically coupled to the connector and a distal end electrically coupled to a tip electrode at the distal end of the insulative body. A composite wire having a proximal end is electrically coupled to the connector. The composite wire includes an inner conductor element and a plurality of outer conductor elements adjacent to and radially spaced from the inner conductor element. A distal end of each of the inner conductor element and the plurality of outer conductor elements is connected to one of a plurality of pace/sense electrodes in the distal region of the insulative body In Example 17, the medical device lead according to Example 16, wherein each of the plurality of outer conductor elements is substantially parallel to an axis of the inner conductor element.

In Example 18, the medical device lead according to either Example 16 or 17, and further comprising an insulative layer between the inner conductor elements and each of the plurality of outer conductor elements.

In Example 19, the medical device lead according to any of Examples 16-18, and further comprising an encapsulating insulator that covers the plurality of outer conductor elements to electrically isolate the plurality of outer conductor elements from each other.

In Example 20, the medical device lead according to any of Examples 16-19, wherein the connector comprises a feedthrough, and wherein a proximal end of each of the plurality of outer conductor elements is axially staggered on a proximal side of the feedthrough.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 6A-6C illustrate a process for manufacturing a composite wire according to the present disclosure.

Figure 1:
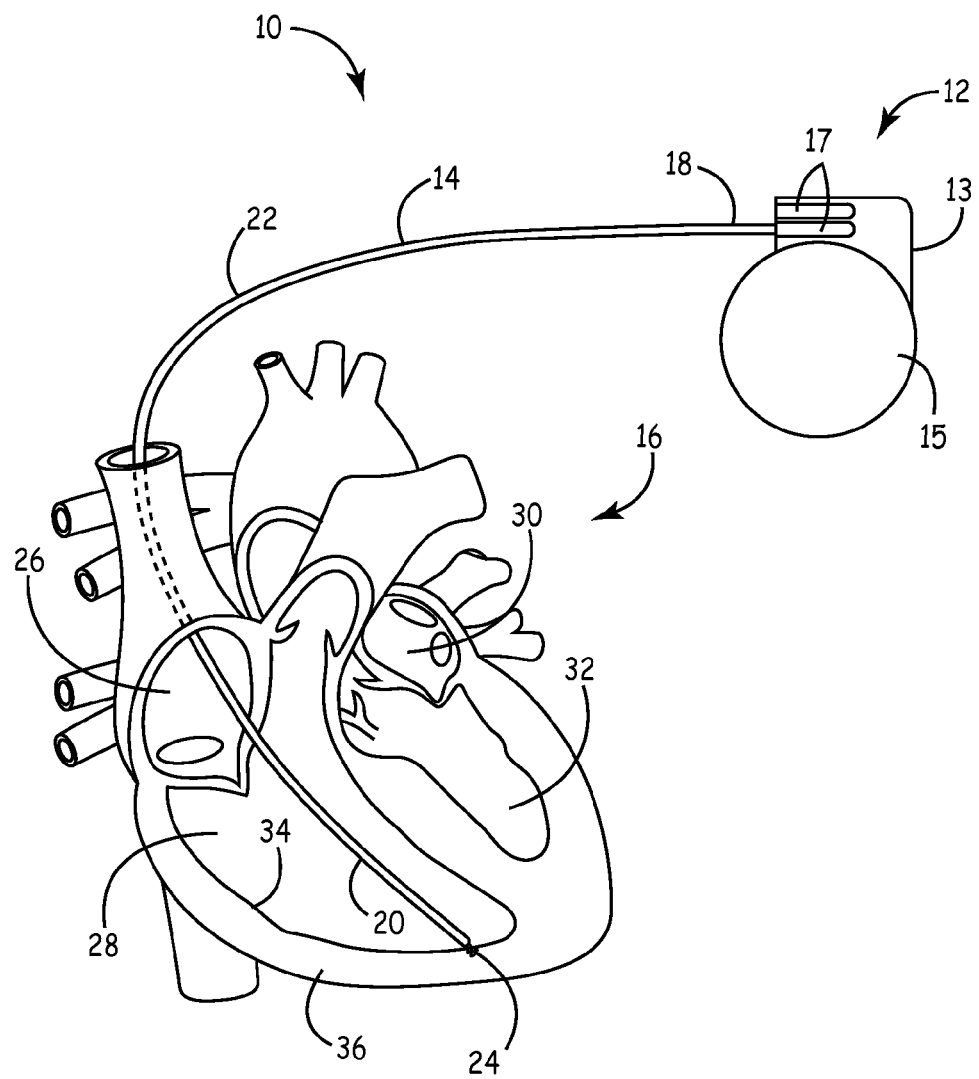
FIG. 1 is a combined cutaway of a heart and a perspective view of an implantable medical device and lead in accordance with one embodiment.

While the invention is amenable to various modifications and alternative forms, specific embodiments have been shown by way of example in the drawings and are described in detail herein. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable medical device (IMD) 10 in accordance with one embodiment. The IMD 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body, or flexible body 22, extending from the proximal region 18 to the distal region 20. The proximal region 18 is coupled to the pulse generator 12 and the distal region 20 is coupled to the heart 16. The distal region 20 includes an extendable/retractable fixation helix 24, which will be discussed in greater detail with respect to subsequent drawings, and which locates and/or secures the distal region 20 within the heart 16. In one alternative embodiment, the distal region 20 includes a plurality of tines or other structures for fixation of the lead 14 relative to the heart 20 (e.g., in a coronary vein or ventricular trabeculae). In another alternative embodiment, the lead 14 is configured as a neural lead including electrode cuffs for coupling the lead 14 to a nerve, or configured for insertion into a spinal cord.

The distal region 20 of the lead 14 has an axially compact design that accommodates a dedicated bipolar electrode configuration. The lead 14 may alternatively have other electrode configurations. As will be explained in further detail herein and shown in additional figures, one or more conductors that electrically couple the connector in the proximal region 18 of the lead 14 to one or more electrodes in the distal region 20 of the lead include a multipolar wire having a plurality of conductive elements.

The pulse generator 12 typically includes a connector header 13 that couples the pulse generator 12 to the lead 14. The connector header 13 typically contains one or more bores 17 that is/are able to receive a connector (not shown) that is part of a connector assembly (not shown, but see 40 in FIG. 2, discussed herein) formed near the proximal region 18 of the lead 14, wherein electrical contacts (not shown) of the connection header 13 couple with lead contacts (not shown) of the connector assembly (not shown).

The connection header 13 can be attached to a hermetically sealed enclosure 15 that contains a battery, electronic circuitry, and other components known to those skilled in the art. Electrical contacts (not shown) in the connection header 13 can be a type known to those skilled in the art that are electrically connected via feedthroughs (not shown) mounted to extend through the hermetically sealed enclosure 15 in order to electrically couple the lead 14 with pulse generator 12.

The pulse generator 12 can be implanted subcutaneously within an implantation location or pocket in the patient's chest or abdomen. In embodiments in which the lead 14 is a neural lead, the pulse generator may alternatively be implanted at the patient's back or buttocks. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from a flexible, biocompatible material suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body 22 characteristics to its intended clinical and operating environments. In various embodiments, proximal and distal ends of the lead body 22 are made from different materials selected to provide desired functionalities.

The heart 16 includes a right atrium 26, a right ventricle 28, a left atrium 30 and a left ventricle 32. The heart 16 includes an endothelial inner lining or endocardium 34 covering the myocardium 36. In some embodiments as illustrated, the fixation helix 24, located at the distal region 20 of the lead, penetrates through the endocardium 34, and is imbedded within the myocardium 36. Alternatively, the lead 14 may be configured as a passive fixation lead as discussed herein. In one embodiment, the IMD 10 includes a plurality of leads 14. For example, it may include a first lead 14 adapted to convey electrical signals between the pulse generator 12 and the right ventricle 28, and a second lead (not shown) adapted to convey electrical signals between the pulse generator 12 and the right atrium 26. Additional leads may also be employed. For example, in various embodiments, a coronary venous lead (not shown) may be utilized for stimulating a left atrium 30 and/or a left ventricle 32 of the heart 16.

In the illustrated embodiment shown in FIG. 1, the fixation helix 24 penetrates the endocardium 34 of the right ventricle 28 and is imbedded in the myocardium 36 of the heart 16. In some embodiments, the fixation helix 24 is electrically active and thus can be used to sense the electrical activity of the heart 16 or to apply a stimulating pulse to the right ventricle 28. In other embodiments, the fixation helix 24 is not electrically active. In still other embodiments, the lead 14 is fixed relative to the heart 16 using passive structures (e.g., tines, spirals, etc.).

During operation, the lead 14 can be configured to convey electrical signals between the IMD 12 and the heart 16. For example, in those embodiments in which the IMD 12 is a pacemaker, the lead 14 can be utilized to deliver electrical stimuli for pacing the heart 16. In those embodiments in which the IMD 12 is an implantable cardiac defibrillator, the lead 14 can be utilized to deliver electric shocks to the heart 16 in response to an event such as a heart attack or arrhythmia. In some embodiments, the IMD 12 includes both pacing and defibrillation capabilities.

The electrical signals are carried between the IMD 12 and electrodes at the distal region 20 by one or more conductors extending through the lead 14. The one or more conductors are electrically coupled to a connector suitable for interfacing with the IMD 12 at the proximal region 18 of the lead 14 and to the one or more electrodes at the distal region 20. According to various embodiments, the one or more conductors include at least one composite conductor comprising a multiconductor wire. In some embodiments, the multiconductor wires are configured to deliver low voltage signals to the one or more electrodes.

Figure 2:
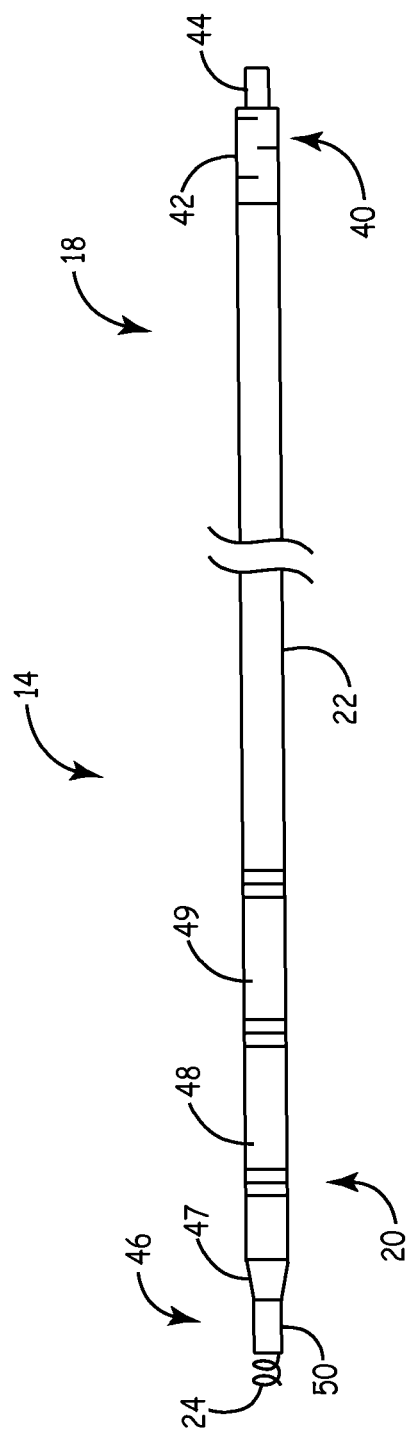
FIG. 2 is a side view of an embodiment of a lead as shown in FIG. 1.

FIG. 2 is an isometric illustration of a lead 14 according to some embodiments. A connector assembly 40 is disposed at or near the proximal region 18, or proximal end, of the lead 14. The connector assembly 40 includes a connector ring 42 and a terminal pin 44. The connector ring 42 is configured to be coupled to the lead body 22 and is configured to mechanically and electrically couple the lead 14 to the header 13 on the pulse generator 12 (see FIG. 1). In various embodiments, the terminal pin 44 extends proximally from the connector ring 42 and in some embodiments is coupled to a conductor member (not visible in this view) that extends longitudinally through the lead body 22 such that rotating the terminal pin 44 relative to the lead body 22 causes the conductor member to rotate within the lead body 22. In some embodiments, the terminal pin 44 includes an aperture (not shown) extending therethrough in order to accommodate a guide wire or an insertion stylet.

A distal assembly 46 is disposed at or near the distal region 20 or distal end of the lead 14 or lead body 22. Depending on the functional requirements of the IMD 10 (see FIG. 1) and the therapeutic needs of a patient, the distal region 20 of the lead 14 may include one or more electrodes. In the illustrated embodiment, the distal region 20 includes one or more coil electrodes 48 and 49 that can function as shocking electrodes for providing, for example, a defibrillation shock to the heart 16. In some embodiments, the coil electrodes 48 and 49 include a coating that is configured to control (i.e., promote or discourage) tissue ingrowth. In various embodiments, the lead 14 may include only a single coil electrode. In various other embodiments, the lead 14 also includes one or more low-voltage electrodes (e.g., ring electrodes), such as electrode 47, along the lead body 22 in lieu of or in addition to the coil electrodes 48, 49. When present, the low-voltage electrodes operate as relatively low-voltage, pace/sense electrodes. As will be appreciated by those skilled in the art, a wide range of electrode combinations may be incorporated into the lead 14 within the scope of the various embodiments.

The distal assembly 46 includes a housing 50, within which the fixation helix 24, or helical electrode, is at least partially disposed. As will be explained in greater detail herein, the housing 50 accommodates a mechanism that enables the fixation helix 24 to move distally and proximally relative to the housing 50, but that includes structure (not seen in this view) that limits distal travel of the fixation helix 24 (relative to the housing 50) in order to reduce or prevent over-extension of the fixation helix 24. As noted herein, the fixation helix 24 operates as an anchoring means for anchoring the distal region 20 of the lead 14 within the heart 16. In alternative embodiments, the lead 14 is fixed relative to the heart 16 using passive structures (e.g., tines, spirals, etc.).

In some embodiments, the fixation helix 24, or helical electrode, is electrically active, and is used as a low-voltage, pace/sense electrode. In some embodiments, the fixation helix 24 is made of an electrically conductive material such as ELGILOY™, MP35N™, tungsten, tantalum, iridium, platinum, titanium, palladium, stainless steel as well as alloys of these materials.

The lead 14 is one exemplary implementation of a lead in accordance with the present disclosure, and other configurations for the lead 14 are also possible. For example, while coil electrodes 48, 49 are shown adjacent to each other, the coil electrode 49 may alternatively be disposed more proximally on the lead 14. As another example, the lead 14 may include a plurality of annular electrodes along the distal region 20 for providing pacing and/or sensing signals to adjacent tissue.

Figure 3A:
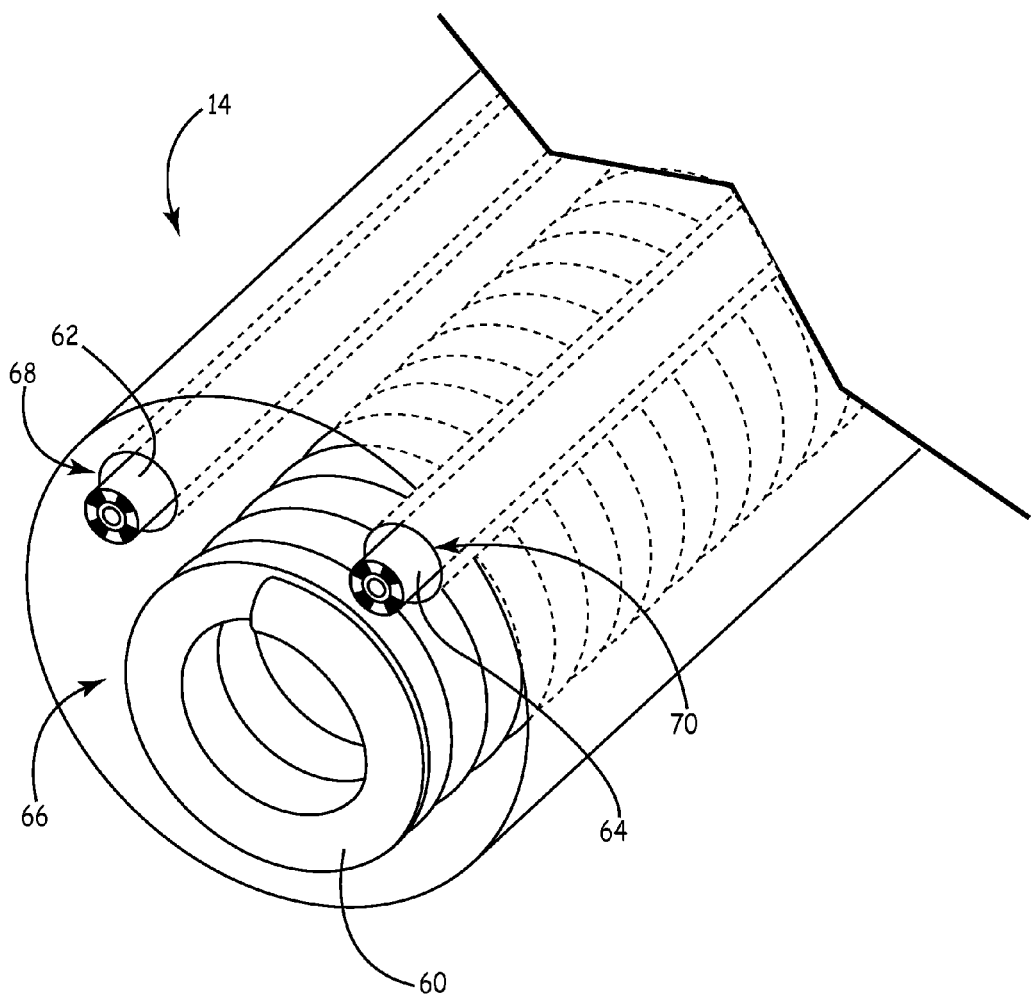
FIG. 3A is a perspective view of a portion of the lead shown in FIG. 1, illustrating multipolar wires according to the present disclosure.
Figure 3B:
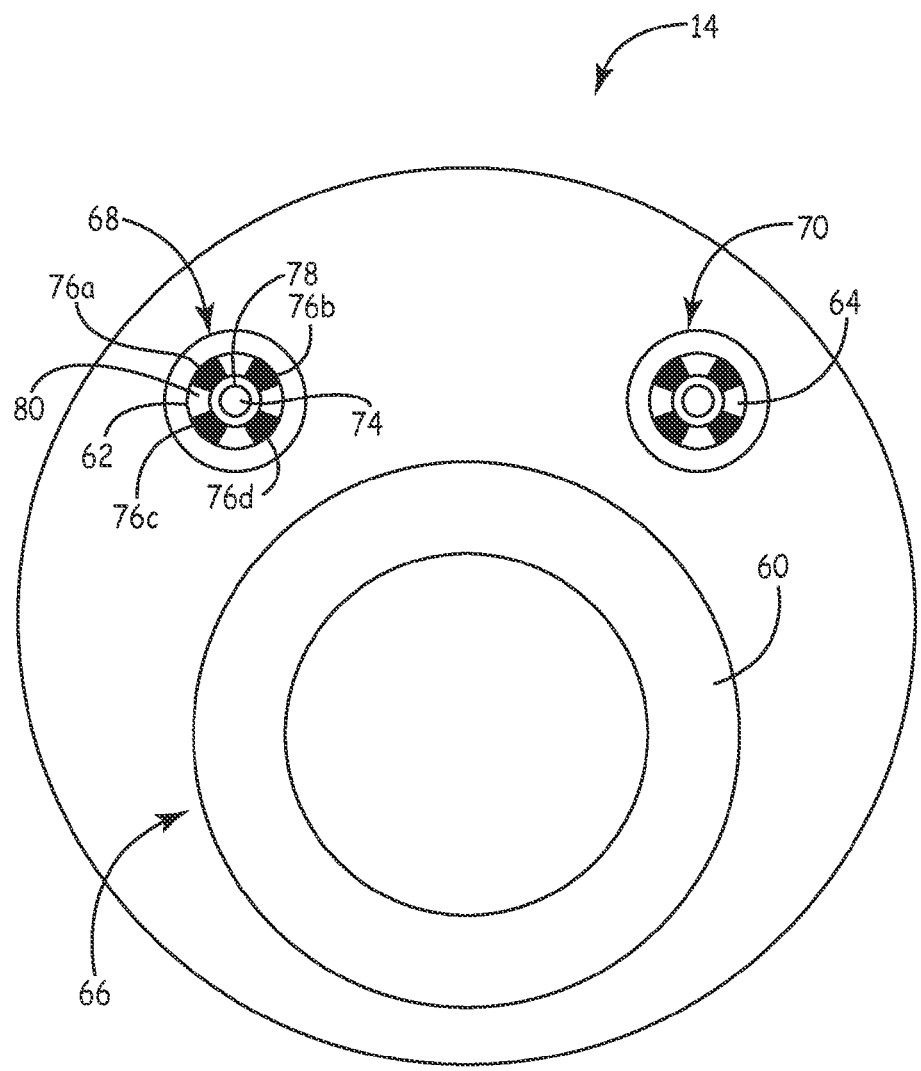
FIG. 3B is a cross-sectional view of a portion of the lead shown in FIG.

FIG. 3A is a cross-sectioned, perspective view, and FIG. 3B is a cross-sectional view, of a portion of the lead 14 according to embodiments of the present disclosure. The lead 14 includes a coil conductor 60 and composite wires 62 and 64. In the illustrated embodiment, the lead 14 includes a lead body having a plurality of lumens 66, 68, and 70. The coil conductor 60 passes through the lumen 66, the composite wire 62 passes through the lumen 68, and the composite wire 64 passes through the lumen 70. In some embodiments, the lumens 66, 68, 70 extend substantially parallel from the connector 40 at the proximal region 18 to the distal region 20.

The coil conductor 60 is adapted for connection to the pulse generator 12 at the proximal region 18 of the lead 14. For example, the coil conductor 60 may be electrically connected to the connector ring 42. In the embodiment shown, the coil conductor 60 extends in parallel through the lead 14 with the composite wires 62, 64. The longitudinal axis of the coil conductor 60 is offset from the longitudinal axes of the composite wires 62, 64. In some embodiments, the coil conductor 60 is electrically coupled to one or more electrodes in the distal region 20 of the lead 14. For example, in some implementations the coil conductor 60 may be electrically coupled to the fixation helix 24 and/or the ring electrode 47. The coil conductor 60 may alternatively or additionally be connected to other electrodes. To reduce the amount of MRI-induced energy that is transmitted to the electrodes connected to the coil conductor 60, the turns of the coil conductor 60 may be tightly wound to maximize the inductance of the coil. In some embodiments, to minimize the space between adjacent turns and maximize the number of turns, the coil conductor 60 is unifilar. In other embodiments, the coil conductor 60 is multifilar.

The composite wires 62, 64 are also adapted for connection to the pulse generator 12 at the proximal region 18 of the lead 14, for example via electrical connection to the connector ring 42. One exemplary implementation of a feedthrough on the connector ring 42 suitable for use with the composite wires 62, 64 is described in more detail herein with regard to FIG. 5. In some embodiments, the composite wires 62, 64 are configured to carry low voltage signals between the pulse generator 12 and one or more electrodes in the distal region 20. For example, with regard to the embodiment of the lead 14 shown in FIG. 2, the composite wires 62 and/or 64 may be connected to the proximal end and/or distal end of the coil electrodes 48, 49. In this way, the composite wires 62, 64 operate to carry sensing and/or pacing signals between the pulse generator 12 and the coil electrodes 48, 49. In alternative embodiments, composite wires 62 and/or 64 may be connected to the ring electrode 47 and/or fixation helix 24. In other embodiments not shown, the composite wires 62, 64 are connected to a plurality of ring electrodes or electrodes having other configurations.

Each of the composite wires 62, 64 includes a plurality of conductor elements configured as a single wire. In the embodiments illustrated, the composite wires 62, 64 each include five conductor elements (identified as conductor elements 74, 76a, 76b, 76c, and 76d of composite wire 62 in FIG. 3B). The conductor elements 74 and 76a-76d are straight filars that extend from the proximal region 18 to the electrodes at the distal region 20. In alternative embodiments, the inner conductor element 74 is configured as a coil. In some embodiments, the conductor elements 74, 76a, 76b, 76c, and/or 76d are comprised of a flexible conductive material, such as Nitinol. Other conductive materials may also be used for the conductor elements 74, 76a, 76b, 76c, and/or 76d, such as MP35N including a silver core. In the embodiment shown, the outer conductor elements 76a-76d each have an inner surface proximate to the inner conductor element 74, and an outer surface on a side opposite the inner surface. In some embodiments, the inner surface has a greater surface area than the outer surface. The outer conductor elements 76a-76d may alternatively be configured to have a different cross-section, such as a circular or oval cross-section.

The outer conductor elements 76a-76d are separated from the inner conductor element 74 by an insulative layer 78. The insulative layer 78 electrically isolates the inner conductor element 74 from the outer conductor elements 76a-76d. The composite wires 62, 64 also include an encapsulating insulator 80 that surrounds the inner conductor elements 76a-76d to electrically isolate the inner conductor elements 76a-76d from each other. In some embodiments, the insulative layer 78 and/or encapsulating insulator 80 may be comprised of a polymeric material including, but are not limited to, expanded polytetrafluoroethylene (ePTFE), layered ePTFE, polytetrafluoroethylene (PTFE), polyethylene terephthalate (PETE), ethylene/tetrafluoroethylene copolymer (ETFE), fluorinated ethylene propylene (FEP), polyether ether ketone (PEEK), fluorinated ethylene propylene (FEP), perfluoro-alkoxy (PFA), and polyvinylidene fluoride (PVDF), polyamides, polyimides, para-aramid synthetic fibers, polyurethane, or polyisobutylene polyurethane (PIB PUR). The encapsulating insulator 80 may be shaped to provide composite wires 62, 64 having cross-sectional shape suitable for the lumens 68, 70. For example, in the embodiments shown, the composite wires 62, 64 have a substantially circular cross-sectional shape to fit in the substantially circular lumens 68, 70.

While two composite wires 62, 64 are shown, the lead 14 may alternatively include any number of composite wires. In one alternative configuration, the lead 14 includes at least one composite wire and a plurality of annular electrodes in the distal region, and at least one of the conductive elements on the composite wire is connected to each of the plurality of annular electrodes. In addition, while the composite wires 62, 64 include five conductor elements 74 and 76a-76d in the embodiment shown, the composite wires 62, 64 may alternatively include more or fewer conductor elements.

In some embodiments, the inner conductor 74 has a diameter of less than about 0.003 inch (0.0762 millimeter (mm)), and the plurality of outer conductor elements has a height of less than about 0.010 inch (0.254 mm). In some embodiments, the overall diameter of the lead 14 is between about 5 and 6 French (1.67 to 2.0 mm).

Figure 4:
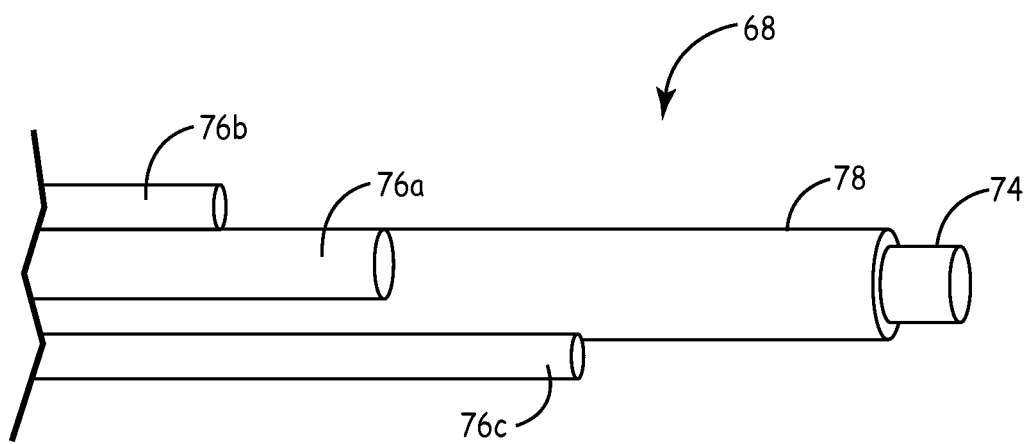
FIG. 4 is a side view of a proximal end of a composite wire according to the present disclosure.
Figure 5:
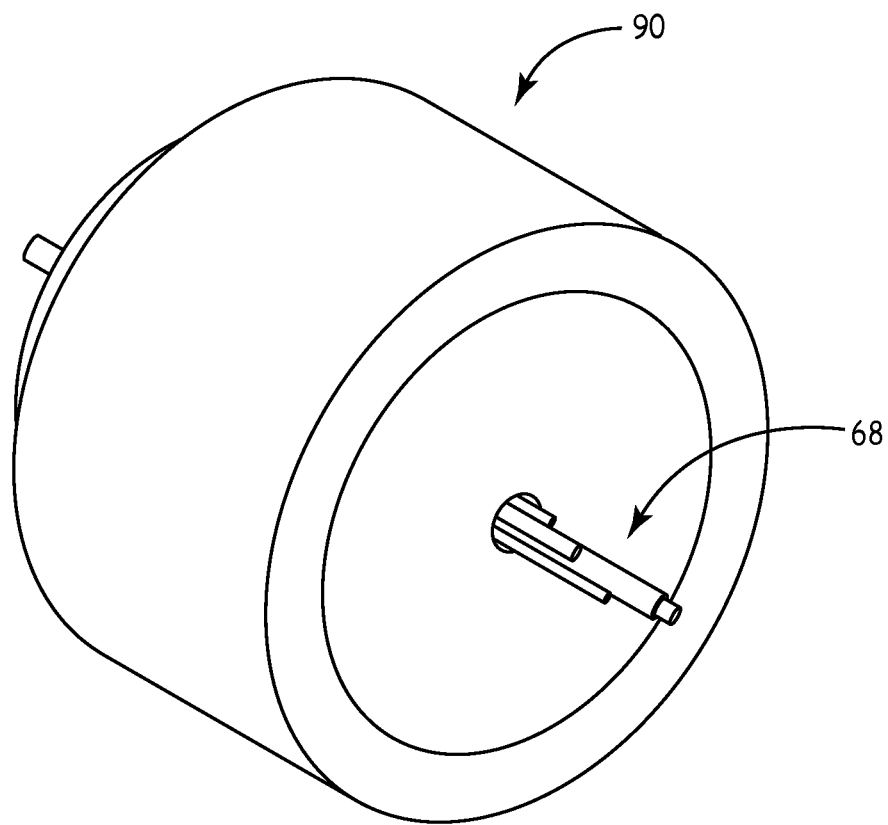
FIG. 5 is a perspective view of a feedthrough portion of a connector including the proximal end of the composite wire.

FIG. 4 is a side view of proximal end of composite wire 68 according to embodiments of the present disclosure. The encapsulating insulator 80 has been omitted in FIG. 4 to more clearly illustrate the configuration of the conductor elements 74 and 76a-76d. In some embodiments, the proximal end of the composite wire 68 passes through a feedthrough in the connector 40. For example, FIG. 5 is a side view of the proximal end of the composite wire 68 passing through a feedthrough 90. On the proximal side of the feedthrough, the conductor elements 74 and 76a-76d are electrically coupled to contact elements on the connector 40 to provide a conduit for electrical connection between the pulse generator 12 and the conductor elements 74 and 76a-76d. In the illustrated embodiment, the proximal ends of the outer conductors 76a-76d are axially staggered with respect to each other such that the proximal ends of the outer conductors 76a-76d are at varied distances from the proximal end of the composite wire 68. This provides space between the proximal ends of the outer conductor elements 76a-76d to prevent arcing between the outer conductor elements 76a-76d, for example at the points of connection to the connector 40. In some embodiments, the proximal ends of the outer conductor elements 76a-76d are laser ablated to the preferred lengths for connection to the connector 40.

FIGS. 6A-6C illustrate a process for manufacturing a composite wire 68 or 70 according to the present disclosure. In FIG. 6A, the insulative layer 78 is formed over the inner conductor element 74 such that the insulative layer 78 defines a tube that covers the outer surface of the inner conductor element 74. A tube of insulative material may be drawn over the inner conductor element 74 to form the insulative layer 78. Alternatively, the insulative layer 78 may be sputtered or deposited onto the outer surface of the inner conductor element 74. The assembly of the inner conductive element 74 and insulative layer 78 may then be processed to size and shape the assembly. An outer conductive layer 95 is then formed over the insulative layer 78, such as by drawing a tube of conductive material over the insulative layer 78, or by depositing or sputtering.

In FIG. 6B, portions of the outer conductive layer 95 are removed to create separate outer conductor elements 76a-76d. The outer conductive layer 95 is removed to the insulative layer 78 to electrically and mechanically separate the outer conductor elements 76a-76d from each other. In some embodiments, the portions of the outer conductive layer 95 are removed by laser ablating, using abrasives, machining, or other techniques. The technique used to remove the outer conductive layer 95 between the outer conductor elements 76a-76d may be selected to provide outer conductor elements 76a-76d having a desired shape, size, and number.

In FIG. 6C, the encapsulating insulator 80 is formed over the assembly of the inner conductor element 74, insulative layer 78, and outer conductor elements 76a-76d such that the outer conductor elements 76a-76d are electrically isolated from each other. In some embodiments, the encapsulating insulator 80 is extruded over or deposited onto the assembly of the inner conductor element 74, insulative layer 78, and outer conductor elements 76a-76d. In other embodiments, the assembly of the inner conductor element 74, insulative layer 78, and outer conductor elements 76a-76d is dip coated with the encapsulating insulator 80. When the encapsulating insulator 80 has been formed, the assembly may be processed to form the composite wire 68 into the desired shape and size.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device lead comprising:
   a flexible body having a proximal region with a proximal end, and a distal region with a distal end;
   a connector coupled to the proximal end of the flexible body of the lead to electrically and mechanically connect the lead to an implantable pulse generator;
   a plurality of electrodes in the distal region of the flexible body; and
   a composite wire having a proximal end electrically coupled to the connector, the composite wire including:
      an inner conductor element;
      a plurality of outer conductor elements; and
      an insulative layer that is adjacent to and circumferentially surrounds the inner conductor element the insulative layer having an outer circumferential surface,
      wherein a distal end of each of the inner conductor element and the plurality of outer conductor elements is connected to one of the plurality of electrodes, each of the plurality of outer conductor elements includes an inner surface adjacent to the insulative layer and an outer surface on a side opposite the inner surface, a surface area of the inner surface is less than a surface area of the outer surface, the insulative layer is located radially between the inner conductor element and each of the plurality of outer conductor elements, and the entire inner surface of each of the plurality of outer conductor elements is located radially outward from and in direct contact with the outer circumferential surface of the insulative layer.

2. The medical device lead of claim 1, wherein each of the plurality of outer conductor elements is substantially parallel to an axis of the inner conductor element.

3. The medical device lead of claim 1, and further comprising:
   an encapsulating insulator that covers the plurality of outer conductor elements to electrically isolate the plurality of outer conductor elements from each other.

4. The medical device lead of claim 1, wherein the connector comprises a feedthrough, and wherein a proximal end of each of the plurality of outer conductor elements is axially staggered on a proximal side of the feedthrough.

5. A composite wire for an implantable medical device, the composite wire comprising:
   an inner conductor element;
   a plurality of outer conductor elements; and
   an insulative layer that is adjacent to and circumferentially surrounds the inner conductor element the insulative layer having an outer circumferential surface,
   wherein a distal end of each of the inner conductor element and the plurality of outer conductor elements is configured for connection to an electrode, each of the plurality of outer conductor elements includes an inner surface adjacent to the insulative layer and an outer surface on a side opposite the inner surface, a surface area of the inner surface is less than a surface area of the outer surface, the insulative layer is located radially between the inner conductor element and each of the plurality of outer conductor elements, and the inner surface of the each of the plurality of outer conductor elements is located radially outward from and the entire inner surface is in direct contact with the outer circumferential surface of the insulative layer.

6. The composite wire of claim 5, wherein each of the plurality of outer conductor elements is substantially parallel to an axis of the inner conductor element.

7. The composite wire of claim 5, and further comprising:
   an encapsulating insulator that covers the plurality of outer conductor elements to electrically isolate the plurality of outer conductor elements from each other.

8. The composite wire of claim 7, wherein the encapsulating insulator has an outer diameter of less than 0.26 inch (0.66 mm).

9. The composite wire of claim 5, wherein the inner conductor element has a diameter of less than 0.003 inch (0.0762 mm) and plurality of outer conductor elements has a height of less than 0.010 inch (0.254 mm).

10. A medical device lead comprising:
    a flexible body having a proximal region with a proximal end, and a distal region with a distal end;
    a connector coupled to the proximal end of the flexible body of the lead to electrically and mechanically connect the lead to an implantable pulse generator;
    a tip electrode at the distal end of the flexible body;
    a coil conductor having a proximal end electrically coupled to the connector and a distal end electrically coupled to the tip electrode;
    a plurality of pace/sense electrodes in the distal region of the flexible body; and
    a composite wire having a proximal end electrically coupled to the connector, the composite wire including:
       an inner conductor element;
       a plurality of outer conductor elements; and
       an insulative layer that is adjacent to and circumferentially surrounds the inner conductor element the insulative layer having an outer circumferential surface,
       wherein a distal end of each of the inner conductor element and the plurality of outer conductor elements is connected to one of the plurality of pace/sense electrodes, each of the plurality of outer conductor elements includes an inner surface adjacent to the insulative layer and an outer surface on a side opposite the inner surface, a surface area of the inner surface is less than a surface area of the outer surface, the insulative layer is located radially between the inner conductor element and each of the plurality of outer conductor elements, and the inner surface of each of the plurality of outer conductor elements is located radially outward from the outer circumferential surface of the insulative layer and the entire inner surface of each of the plurality of outer conductor elements is in direct contact with the outer circumferential surface of the insulative layer.

11. The medical device lead of claim 10, wherein each of the plurality of outer conductor elements is substantially parallel to an axis of the inner conductor element.

12. The medical device lead of claim 10, and further comprising:
an encapsulating insulator that covers the plurality of outer conductor elements to electrically isolate the plurality of outer conductor elements from each other.

13. The medical device lead of claim 10, wherein the connector comprises a feedthrough, and wherein a proximal end of each of the plurality of outer conductor elements is axially staggered on a proximal side of the feedthrough.

* * * * *